United States Patent [19]

Chen et al.

[11] 4,267,123
[45] May 12, 1981

[54] METHOD OF PREPARING PROPANE SULFONATES

[75] Inventors: Catherine S. H. Chen, Berkeley Heights; Kirk D. Schmitt, Pennington; Albert L. Williams, Princeton, all of N.J.

[73] Assignee: Mobil Oil Corporation, New York, N.Y.

[21] Appl. No.: 96,947

[22] Filed: Nov. 23, 1979

[51] Int. Cl.³ .................. C07C 143/14; C07C 143/38
[52] U.S. Cl. ........................... 260/501.12; 260/512 R; 260/512 C; 260/513 R; 260/513 B
[58] Field of Search .......... 260/501.12, 512 R, 512 C, 260/513 B, 513 R

[56] References Cited

U.S. PATENT DOCUMENTS 3,418,239  12/1968  Cooper ........................... 260/512 R
3,888,917  6/1975  Fentress et al. .................. 260/513 B

OTHER PUBLICATIONS

Wagner & Zook, Synthetic Organic Chem., John Wiley & Sons, N.Y., pp. 226–229, 666–668, 813–814, (1965).
Sittig, Detergent Manufacture, Noyes Data Corp., N.J., pp. 189–193, (1976).
Kominski et al., J. American Oil Chem. Soc., 54, No. 11, pp. 516–520, (1977).

Primary Examiner—Natalie Trousof
Assistant Examiner—G. T. Breitenstein
Attorney, Agent, or Firm—Charles A. Huggett; Michael G. Gilman; Howard M. Flournoy

[57] ABSTRACT

An improved method for preparing propane sulfonates by the addition of metal bisulfites to allyl ethers, amines and sulfides is provided wherein a substantial amount of the desired product is added to the reaction mixture.

9 Claims, No Drawings

METHOD OF PREPARING PROPANE SULFONATES

BACKGROUND OF THE INVENTION

1. Field of the Invention

This application is directed to an improved method of preparing propane sulfonates. Propane sulfonates are highly useful as surfactants or surface active agents and having high tolerance for brine makes such agents especially useful in tertiary oil recovery processes.

2. Description of the Prior Art

Propane sulfonates of various amines and polyethoxylated alcohols are known surfactants. However, propane sulfonates of alcohols and thiols have only been prepared in the literature by reaction of alkali metal salts of the alcohols or thiols with propane sultone. This is a convenient high yield laboratory synthesis but is not desirable on a large scale for several reasons. Foremost among them are the fact that (1) such a reaction requires multistep synthesis and purification of propane sultone (2) propane sultone is expensive to purify and its overall yield of 80–90% limits the yield in the preparation of propane sulfonates and (3) propane sultone is a known carcinogen. Therefore processes involving the use of propane sultone must utilize expensive controls to minimize worker exposure and despite such controls its use will always engender some risk of worker exposure. Because of its carcinogenicity all waste products must be carefully treated to ensure no residues remain. This extra care coupled with the expensive synthesis and purification of propane sultone further increases the desire and need for an alternative means of making propane sulfonates.

The preparation of allyl ethers, sulfides, or amines is well known in the literature, however, the use of the two step procedure described herein to convert alcohols or thiols to propane sulfonates as far as is known to applicants is unknown. One report appears in the literature of an attempt at a similar process for the preparation of propane sulfonates of tertiary amines [*J. Amer. Oil Chem. Soc.*, 53, 60 (1976)] but it reports the process produces excessive quantities of undesirable "iso-sulfonate" whose presence degrades the performance of the product. This readily demonstrates that the overall conditions we employ are novel and unobvious.

The reaction of $MHSO_3$ (M is any suitable metal) with simple olefins has been much studied. The literature teaches that for simple water-soluble olefins or olefins which can be made soluble by the addition of small amounts of alcohols all that is required for high conversion to products are conditions in which all reagents are dissolved in a single phase. We find that the allyl-heteroatom compounds do not behave this way. Conditions may be found in which all the reagents are dissolved in a single phase in alcohol and water and yet the conversion will not exceed 40 or 50% unless a minimum amount of sulfonate as disclosed herein is added. When the propane sulfonate is added the conversion is rarely below 90%.

The early literature on the reaction of $MHSO_3$ with olefins indicated that S-alkylation leading to sulfonate products might be accompanied by a slight amount of O-alkylation leading to sulfites but even this slight formation was disputed and the literature for the last thirty years reveals that sulfites are not by-products in the sulfitation of olefins. We find it surprising that sulfitation of allyl-hetero compounds can produce as great as 100% sulfite in solvents taught in the literature to be acceptable for sulfitation of ordinary olefins to sulfonates. A high yield of sulfite would be surprising because the literature teaches that solvent systems which produce high conversions of olefins will produce high yields of sulfonates.

SUMMARY OF THE INVENTION

Generally the propane sulfonates, D, where R is such that the solubility of C in water is less than 0.5%, X is a heteroatom, and Y is halogen or tosylate, are prepared in a two-step process described below in close to 100% yield by novel control of reaction conditions in Step (2) thereof.

The first step may be carried out in two different ways depending on whether one starts with an alcohol or thiol or tertiary amine. If an alcohol or thiol is used (X=O,S), a base is needed to achieve reaction with the allylhalide or tosylate as shown in reaction (1a). If a tertiary amine is the reagent (X=N), no base is needed as shown in (1b).

RXH + Base + CH$_2$=CHCH$_2$Y ⟶   (1a)

A                      B

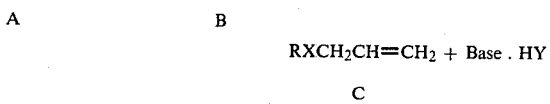

RXCH$_2$CH=CH$_2$ + Base · HY

C

RXCH$_2$CH=CH$_2$ + HMSO$_3$ ⟶ RXCH$_2$CH$_2$CH$_2$SO$_3$M or   (2a)

C                                        D

R$_3$X + CH$_2$=CHCH$_2$Y ⟶ R$_3$N$^+$CH$_2$CH=CH$_2$ Y$^-$   (1b)

A        B               C

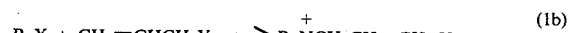

R$_3$N$^+$CH$_2$CH=CH$_2$ Y$^-$ + HMSO$_3$ ⟶ R$_3$N$^+$CH$_2$CH$_2$CH$_2$SO$_3^-$   (2b)

C                                   D

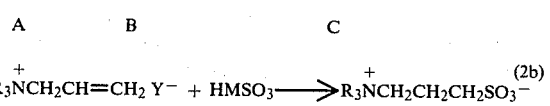

The reaction of step (1a) or (1b) is well known in the literature. Step (2a) or (2b) is carried out by addition of a buffered solution of $MHSO_3$ to an aqueous alcoholic solution containing both allyl compound C and a certain minimum amount of desired final product D while stirring vigorously and passing a slow stream of air or oxygen through the reaction vessel. The rate of flow of air or oxygen is not critical. The minimum molar ratio of final product D to allyl compound C is 1/5. All small water-soluble alcohols, e.g., methanol, ethanol, may be used. Tertiary-butyl alcohol, ethanol and 1-propanol are the preferred alcohols. A convenient method to minimize the amount of final product which must be used is to charge the reaction vessel with only a portion of the allyl compound, and enough final product to make the minimum 1/5 ratio and then to add the remaining allyl compound while the $MHSO_3$ solution is added at a rate to ensure the ratio of final product to allyl compound in the vessel is always greater than 1/5. The reactions are generally carried under ambient conditions of temperature and pressure although higher pressures and temperatures may be used if desired.

R can be $C_6$ to $C_{16}$ alkyl, alkenyl or alkynyl, and aryl of from 6 to 20 carbon atoms. R may also represent an alkyl or aryl polyethoxy group selected from R'O—(CH$_2$CH$_2$O)n— and

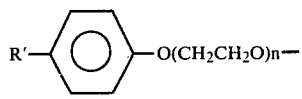

where R'=$C_6$-$C_{20}$ n=1-13.

M is any suitable metal, or $NH_4^+$, although alkali metals particularly sodium and lithium are preferred.

Suitable heteroatoms (X) include oxygen, nitrogen, and sulfur.

Y as stated above is halogen (halide) or tosylate. Y is preferably $Cl^-$ or $Br^-$.

Allyl heteroatom compounds such as 3a are generally prepared by refluxing an equimolar mixture of a commercially available polyethoxynonylphenol, and metallic sodium in toluene until all the sodium dissolved, then adding two equivalents of allyl chloride and refluxing until analysis by high pressure liquid chromatography (HPLC, described below) shows no more than 2% of the polyethoxynonylphenol remained.

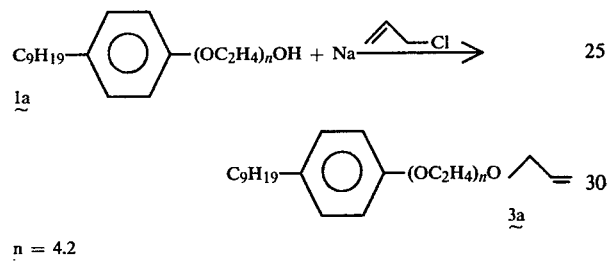

n = 4.2

DESCRIPTION OF SPECIFIC EMBODIMENTS

The following examples illustrate the conditions set forth herein above for obtaining high conversions and high yields from the allyl compounds.

EXAMPLE 1

Example 1 illustrates that high conversion of the allyl hetero compound may be achieved without high yields and describes the analytical procedures which establish the structure of the sulfite product. A one liter 4-neck flask equipped with a mechanical stirrer was charged with 120 ml. methanol, 75 ml. $H_2O$, 27 g sulfonate (4a)

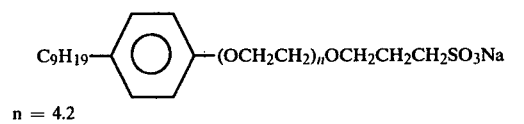

n = 4.2 and 66.9 g allyl ether. A homogeneous solution resulted which was stirred at about 800–1000 RPM while air was passed through the flask at about 15 ml/min and a solution of 18.72 g $NaHSO_3$ and 11.34 g $Na_2SO_3$ in 69 ml $H_2O$ was added dropwise over about one hour. Stirring was stopped occasionally and the reaction mixture analyzed by HPLC on a Water's Associates μ-Bondapak C-18 column using 0.005 M $Bu_4N^{30}H_2PO_4^-$ in 86% methanol—14% $H_2O$ as eluant. A UV detector set for 277 nm was used. Since each of the compounds has the same UV chromophore with λmax.=277 nm the output of the detector could be translated directly into mole percent. As the reaction proceeded the temperature rose exothermally about 5° C. Analysis by HPLC showed three materials with retention volumes 4.3 ml., 6.7 ml., and 34.3 ml. The second and third peaks had retention volumes identical to sulfonate 4a and the allyl compound respectively. Within two hours of the start of the reaction HPLC analysis indicated 95% of the allyl compound to be reacted but only 14–15% of this had been converted to sulfonate 4a. The rest had been converted into sulfite 5a (described below) whose structure was shown by $^{13}C$ NMR and chemical degradation.

The reaction was let stand overnight then filtered from precipitated inorganic salts, evaporated on a rotary evaporator and a $^{13}C$ NMR obtained. In addition to the peaks expected for 4a (by comparison to a spectrum of authentic 4a) two additional peaks due to one carbon each were seen at 62.9 ppm and 25.1 ppm. These are assigned to the $NaO_2S$—O—$CH_2$—$CH_2$— carbons of sulfite 5a.

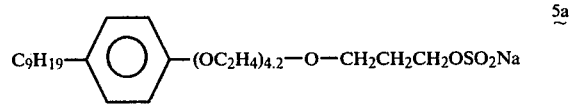

That this material is the sulfite was shown by heating the reaction product at 60° C. at 0.05 mm Hg for four hours. A gas was collected in a dry ice trap. Infrared annalysis showed this gas to be sulfur dioxide. Carbon-13 NMR of the remaining material in moist $CDCl_3$ shows the peak at 62.9 ppm to be gone and a new peak at 57.4 ppm to have appeared. This new chemical shift is identical to that of 3-methoxy-1-propanol. These results are summarized by reaction (4).

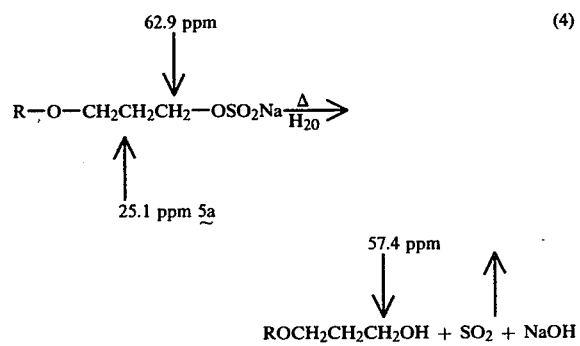

EXAMPLE 2

The same reaction as Example 1 was carried out with ethanol substituted for methanol. After three hours the conversion of allyl ether 3a was 99% and the yield of sulfonate was not 14% as in Example 1 but 92%.

EXAMPLE 3

The same reaction as Example 1 was carried out but 1-propanol was substituted for methanol. The conversion after three hours was 94% and the yield 85%.

EXAMPLE 4

The same reaction was Example 1 was carried out but 2-propanol was substituted for methanol. The conversion after three hours was 99% and the yield 84%.

EXAMPLE 5

The same reaction as Example 1 was carried out but water was substituted for methanol. The conversion after three hours was 96% and the yield 3%.

EXAMPLE 6

The same reaction as Example 2 was carried out but only 5.67 g Na$_2$SO$_3$ were used. The conversion after three hours was 90% and the yield 78%.

EXAMPLE 7

The reaction of Example 2 was repeated but no sulfonate 4a was added initially. A homogeneous solution did not result. After three hours there was no reaction.

EXAMPLE 8

The reaction of Example 2 was repeated but 15 g sulfonate were used. The ratio of sulfonate to allyl compound was 0.189. The reaction mixture was homogeneous. After three hours the conversion was 87% and the yield 72%.

EXAMPLE 9

The reaction of Example 2 was repeated but 9 g sulfonate were used. The reaction mixture was not homogeneous. The ratio of sulfonate to allyl compound was 0.113. After three hours the conversion was 40% and the yield 3%.

EXAMPLE 10

The reaction of Example 2 was repeated but the NaHSO$_3$ and Na$_2$SO$_3$ were added as solids all at once to the homogeneous solution already containing the 69 ml H$_2$O. The conversion after three hours was 71% and the yield 6%.

EXAMPLE 11

The reaction of Example 2 was repeated but tertiary-butyl alcohol was substituted for methanol. The conversion after three hours was 99% and the yield 86%.

EXAMPLE 12

The reaction was carried out as in Example 3, but 36 g of heptaethoxydinonylphenol were used instead of 1a, and 68.6 g of the allyl ether of this heptaethoxy alcohol were used instead of 3a. The conversion after three hours was 97% and the yield was 90%.

The examples clearly illustrate that the reactants and reaction conditions are all important in achieving the desired product in high conversion and high yield. Note, for example, the yield of the desired product in Example 1 versus that for Examples 2, 3 and 4. Note also that when water as in Example 5 was substituted for the alcoholic reactant, although conversion was 96% yield was only 3% and that when the reaction mixture was not homogeneous as in Example 9 conversion was only 40% and yield only 3%.

As readily apparent to one of ordinary skill in the art variations and departures from the exemplary matter disclosed herein can be readily made and are within the scope of this invention.

We claim:

1. A method of preparing propane sulfonates comprising the following two step reactions:

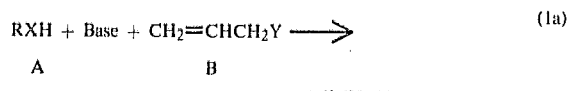

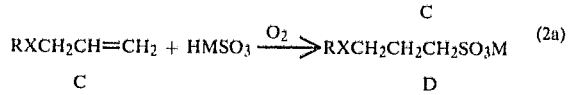

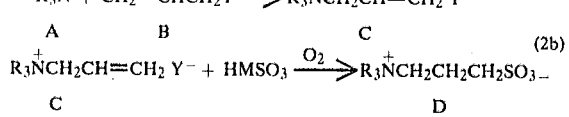

where X is O or S in (1a) and (2a), M is NH$_4^+$ or an alkali metal and R is C$_6$–C$_{16}$ alkyl, alkenyl or alkynyl and C$_6$–C$_{20}$ aryl, or C$_6$–C$_{20}$ alkyl or aryl —O—(CH$_2$CH$_2$O)n— in which n=2–13 and Y is halide or tosylate and where a predetermined minimum amount of final product D in a molar ratio of D to compound C of at least 1 to 5 is initially added to the reaction mixture of Step (2a) and (2b).

2. The method of claim 1 wherein a first portion of compound C is added to said reaction mixture and then sufficient final product D is added thereto to meet said minimum 1 to 5 ratio and thereafter adding additional final product D at a rate which ensures said ratio will always be greater than 1 to 5.

3. The method of claims 1 or 2 wherein M is lithium or sodium.

4. The method of claim 3 wherein M is sodium.

5. The method of claims 1 or 2 wherein Y is Cl$^-$ or Br$^-$.

6. The method of claim 5 wherein Y is Cl$^-$.

7. The method of claims 1 or 2 wherein the desired final product is

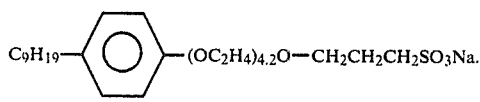

8. The method of claims 1, 2 or 3 wherein Step (2) is carried out by the addition of a buffered solution of a suitable amount of HMSO$_3$ to an aqueous alcoholic solution containing said compound C and said minimum amount of final product D while passing a stream of air or oxygen, at a rate sufficient to facilitate the reaction, through the reaction mixture.

9. The method of claim 8 wherein the alcohol is selected from t-butanol, ethanol, 2-propanol and 1-propanol.

* * * * *

UNITED STATES PATENT AND TRADEMARK OFFICE
CERTIFICATE OF CORRECTION

PATENT NO. : 4,267,123

DATED : May 12, 1981

INVENTOR(S) : Catherine S.H. Chen, et al

It is certified that error appears in the above–identified patent and that said Letters Patent are hereby corrected as shown below:

Col. 3, line 62      "$Bu_4N^{3O}H_2PO_4$" should be --$Bu_4N^+H_2PO_4$--

Signed and Sealed this

Fifth Day of January 1982

[SEAL]

Attest:

GERALD J. MOSSINGHOFF

Attesting Officer     Commissioner of Patents and Trademarks